United States Patent [19]

Pavan et al.

[11] 4,277,408

[45] Jul. 7, 1981

[54] NOVEL PURIFICATION PROCESS

[75] Inventors: Charles Pavan, Nogent-sur-Marne; Jacques Bulidon, Paris, both of France

[73] Assignee: Roussel Uclaf, Paris, France

[21] Appl. No.: 97,710

[22] Filed: Nov. 27, 1979

[30] Foreign Application Priority Data

Dec. 11, 1978 [FR] France ................. 78 34767

[51] Int. Cl.$^3$ ............................................. C07J 9/00
[52] U.S. Cl. .................................................. 260/397.1
[58] Field of Search ..................................... 260/397.1

[56] References Cited

U.S. PATENT DOCUMENTS

| | | | |
|---|---|---|---|
| 3,965,131 | 6/1976 | Wiele et al. | 260/397.1 |
| 4,022,806 | 5/1977 | Frost et al. | 260/397.1 |
| 4,163,017 | 7/1979 | Maeke et al. | 260/397.1 |

Primary Examiner—Elbert L. Roberts
Attorney, Agent, or Firm—Hammond & Littell, Weissenberger and Muserlian

[57] ABSTRACT

A novel process for the purification of $3\alpha,7\alpha$-dihydroxy-$(5\beta)$-cholanic acid comprising crystallizing the said product from methylene chloride.

8 Claims, No Drawings

NOVEL PURIFICATION PROCESS

STATE OF THE ART

Chenodesoxycholic acid or 3α,7α-dihydroxy-(5β)-cholanic acid permits the dissolution of cholesterolic gallstones and is used in human medicine for the treatment of bile lithiasis. Chenodesoxycholic acid is generally prepared starting from naturally occurring substances and is readily prepared from cholic acid or 3α,7α,12α-trihydroxy-(5β)-cholanic acid which is obtained by extraction of animal bile whereby the 12 hydroxy group is removed by a series of reactions [Feiser et al, J.A.C.S., Vol. 72 (1950), p. 5530].

Raw chenodesoxycholic acid contains from its preparation by-products, especially other bile acids such as lithocholic acid and the presence of these impurities is undesirable as the said product is administered in prolonged therapy and the impurities produce undesired secondary effects. It is therefore important to administer chenodesoxycholic acid in as pure a form as possible.

German application No. 2,302,744 describes the purification of chenodesoxycholic acid by treating a methanol solution of the raw product with a calcium salt or strontium salt under alkaline conditions and treating the resulting calcium or strontium salt of chenodesoxycholic acid with an acid and extracting the acid solution to recover chenodesoxycholic acid. French Pat. No. 2,273,011 describes the purification of raw chenodesoxycholic acid by liquid-liquid extraction of an aqueous solution of an alkali metal salt of the said acid, preferably sodium or potassium, with an organic solvent, preferably ethyl acetate or a mixture of isobutanol and toluene, acidifying the resulting solution with a dilute acid, preferably hydrochloric acid, and adding water to precipitate chenodesoxycholic acid.

French Pat. No. 2,269,957 proposes to purify chenodesoxycholic acid by preparing an inclusion complex of the raw acid and a clathrate of an organic solvent such as ethyl acetate or heptane and then eliminating the organic solvent. French Pat. No. 2,346,370 describes purification of raw chenodesoxycholic acid by crystallization from acetonitrile. Related also is Japanese patent application Ser. No. A53.137945.

OBJECTS OF THE INVENTION

It is an object of the invention to provide a novel industrial process for the purification of chenodesoxycholic acid to obtain a therapeutically pure product devoid of manifestations of intolerance and side effects due to the presence of significant quantities, although very small percentages, of annoying impurities such as lithocholic acid.

It is another object of the invention to provide a purified 3α,7α-dihydroxy-(5β)-cholanic acid.

These and other advantages and objects of the invention will become obvious from the following detailed description.

THE INVENTION

The novel process of the invention for the removal of bile acids from impure chenodesoxycholic acid comprises crystallizing chenodesoxycholic acid containing approximately 2% of other bile acids from a methylene chloride solvent system to obtain a purified chenodesoxycholic acid containing less than 1% of foreign bile acids of which is less than 0.1% lithocholic acid. The process results in a pure chenodesoxycholic acid which may be administered daily to a patient for a period of months. The high degree of purity resulting with satisfactory yields on an industrial scale of the process of the invention could not be attained by the known processes.

The resulting crystalline product of the invention is probably constituted of pure 3α,7α-dihydroxy-5β-cholanic acid in a particular crystalline form or as a solvate of the acid. However, this is only a theory and should not be intended to limit the invention.

The preferred solvent system for the crystallization of the invention is a mixture of methylene chloride and an alcohol, preferably an aliphatic alcohol of 1 to 5 carbon atoms. Examples of suitable alcohols are alkanols such as methanol, ethanol, propanol, isopropanol and butanol, dihydroxy alcohols such as glycol and alkoxy alkanols of 2 to 6 carbon atoms such as ethoxy ethanol.

Preferably the raw 3α,7α-dihydroxy-(5β)-cholanic acid is dissolved in a mixture of ethanol and methylene chloride and then methylene chloride is added thereto. The said crystallization system preferably uses 0.1:1 to 0.7:1 of ethanol and 5.9:1 to 7.2:1 of methylene chloride with respect to the weight of 3α,7α-dihydroxy-(5β)-cholanic acid.

The crystallization is preferably effected with heating, especially at reflux temperatures. The recovered crystalline 3α,7α-dihydroxy-(5β)-cholanic acid is dried, preferably by heating under reduced pressure or with ventilation. The crystalline form of 3α,7α-dihydroxy-(5β)-cholanic acid may be recrystallized from another solvent or solvent system or by dissolution in a solvent or solvent system, especially in a mixture of acetone and water followed by partial evaporation of the solvent or solvent system and recovering the crystalline product.

The novel product of the invention is purified 3α,7α-dihydroxy-(5β)-cholanic acid containing less than 1% impurities and especially less than 0.1% of 3α-hydroxy-cholanic acid. The said purified product is in the form of a crystalline product formed in methylene chloride by the process of the invention.

In the following example there are described several preferred embodiments to illustrate the invention. However it is to be understood that the invention is not intended to be limited to the specific embodiments.

EXAMPLE

A mixture of 100 g of raw chenodesoxycholic acid containing about 2% of impurities consisting essentially of foreign bile acids with about 0.5% of 3α-hydroxy-cholanic acid (lithocholic acid), 40 ml of 100% ethanol denatured of butanol, 210 ml of methylene chloride and 0.1 g of sodium acetate was vigorously stirred at 20°-25° C. until dissolution occurred and the solution was refluxed for 20 minutes. 450 ml of methylene chloride were added with vigorous stirring over 10 minutes to the refluxing solution which caused an abundant crystallization. The mixture was refluxed for one hour and was cooled over 3 hours to 0° to −2° C. The mixture was stirred at 0° to −2° C. for 2 hours and was then vacuum filtered. The recovered product was washed 3 times with a mixture of 2.8 ml of 100% ethanol denatured of butanol and 47.2 ml of methylene chloride at 0° to −2° C. and was dried in a ventilated oven at 40° C. to obtain 79 g of purified chenodesoxycholic acid melting at 123° C. and containing less than 0.1% of methylene chloride. The product was dissolved in 316 ml of acetone containing 5% of water and the mixture was stirred at 20°–25° C. until dissolution occurred. 0.79 g of activated carbon were added to the solution and the mixture was stirred for 15 minutes and was filtered. The filter was rinsed with 79 ml of acetone containing 5% of water and 74.2 ml of water were added to the filtrate. The mixture was heated to reflux and 237 ml of a water-acetone mixture were distilled. 237 ml of water were added to the mixture which was then cooled to 38° C. and was stirred for 2 hours. The mixture was cooled to 20°–22° C., stirred for 2 hours and was vacuum filtered. The recovered product was washed 3 times with 79 ml of water and was dried to obtain 76.6 g of purified chenodesoxycholic acid with a specific rotation of $[\alpha]_D^{20} = +10.5° \pm 1°$ (c=10% in dioxane). The wash waters and the crystallization mother liquor were treated to obtain a second yield.

Thin layer chromatography showed that the purified product contained less than 1% of bile acids other than chenodesoxycholic acid, mainly cholic acid, $3\alpha,7\alpha$-dihydroxy-12-keto-cholanic acid, $3\alpha$-hydroxy-cholanic acid or lithocholic acid and $3\alpha,12\alpha$-dihydroxy-cholanic acid or desoxycholic acid and especially less than 0.1% of lithocholic acid. The thin layer chromatography was effected with silica plates and the chenodesoxycholic acid was used as a 4% solution in acetone.

A 10 μl deposit was effected and the migration solvent used was a 5-5-2 isooctane-ethyl acetate-acetic acid mixture. The migration was effected in a saturated vat to 15 cm and was then continued during one hour. The revelation was caused by spraying with 10% sulfuric acid in ethanol, heating to 100° C. and examining under ultraviolet light.

Various modifications of the process of the invention may be made without departing from the spirit or scope thereof and it should be understood that the invention is to be limited only as defined in the appended claims.

We claim:

1. A process for the preparation of purified $3\alpha,7\alpha$-dihydroxy-$(5\beta)$-cholanic acid comprising crystallizing chenodesoxycholic acid containing approximately 2% of other bile acids from a methylene chloride solvent system to obtain a purified chenodesoxycholic acid containing less than 1% of foreign bile acids of which is less than 0.1% lithocholic acid.

2. The process of claim 1 wherein the solvent system is a mixture of methylene chloride and an alcohol.

3. The process of claim 2 wherein the alcohol is an aliphatic alcohol of 1 to 5 carbon atoms.

4. The process of claim 2 wherein the alcohol is ethanol.

5. The process of claim 4 wherein the ratio is 0.1:1 to 0.7:1 of ethanol and 5.9:1 to 7.2:1 of methylene chloride based on the weight of $3\alpha,7\alpha$-dihydroxy-$(5\beta)$-cholanic acid.

6. The process of claim 1 wherein the crystallization is effected with heating.

7. The process of claim 1 wherein the crystallized product is dried.

8. The process of claim 1 wherein the recovered product is dried, then dissolved in an acetone-water mixture, the solvent is partially evaporated and the crystallized product is recovered.

* * * * *